(12) United States Patent
Manion

(10) Patent No.: US 8,904,851 B2
(45) Date of Patent: Dec. 9, 2014

(54) METHODS AND COMPOSITIONS FOR SENSORS

(75) Inventor: Michael Keoni Manion, Conulla (AU)

(73) Assignee: Empire Technology Development LLC, Wilmington, DE (US)

( * ) Notice: Subject to any disclaimer, the term of this patent is extended or adjusted under 35 U.S.C. 154(b) by 48 days.

(21) Appl. No.: 13/696,689

(22) PCT Filed: Dec. 19, 2011

(86) PCT No.: PCT/US2011/065808
§ 371 (c)(1),
(2), (4) Date: Nov. 7, 2012

(87) PCT Pub. No.: WO2013/095329
PCT Pub. Date: Jun. 27, 2013

(65) Prior Publication Data
US 2013/0152667 A1    Jun. 20, 2013

(51) Int. Cl.
*G01N 33/00* (2006.01)
*G01N 21/64* (2006.01)

(52) U.S. Cl.
CPC ........ *G01N 33/0004* (2013.01); *G01N 21/6486* (2013.01); *G01N 21/6408* (2013.01)
USPC ........................................ 73/31.02; 73/31.03

(58) Field of Classification Search
CPC ................................................ G01N 33/0004
See application file for complete search history.

(56) References Cited

U.S. PATENT DOCUMENTS 4,808,517 A    2/1989  Blondin et al.

FOREIGN PATENT DOCUMENTS

EP    1811298    7/2007
WO    WO 01/68923    9/2001

OTHER PUBLICATIONS

Fabio Erminio Mingatto et al., "Effects of nimesulide and its reduced metabolite on mitochondria", British Journal of Pharmacology,131, pp. 1154-1160, 2000.*
Barbara M. Jordan-Luke, "A Modification of the 'Hermann PO' Method for Mitochondria", Journal of Microscopical Science, vol. 101, part 1, pp. 39-41, Mar. 1960.*
Konstantin G. Lyamzaev et al. "Novel mechanism of elimination of malfunctioning mitochondra (mitoptosis): Formation of mitoptotic bodies and extrusion of mitochondrial material from the cell" Biochimica et Biophysica Acta 1777 (2008) pp. 817-825.*
Da Silva et al., "The use of the Mitochondrial Transmembrane Electric Potential as an Effective Biosensor in Ecotoxicological Research," Chemosphere, 1998, pp. 2375-2390, vol. 36(10).
International Search Report and Written Opinion received in International Application No. PCT/US2011/065808, dated Apr. 18, 2012, filed on Dec. 19, 2011.
Preparing Mitochondria from Rat Liver, information was available at website: http://www.ruf.rice.edu/~bioslabs/studies/mitochondria/mitoprep.html in some form no later than Sep. 26, 2011.
Forster Resonance Energy Transfer, from Wikipedia; information was available at website: http://en.wikipedia.org/wiki/F%C3%B6rster_resonance_energy_transfer in some form no later than Sep. 26, 2011.
Lakowicz, "Principles of Fluorescence Spectroscopy," Plenum Press, New York, 1983.

* cited by examiner

*Primary Examiner* — Paul West
(74) *Attorney, Agent, or Firm* — Knobbe, Martens, Olson, & Bear LLP

(57) ABSTRACT

Provided herein are methods and devices for sensing air quality. In some embodiments, materials from mitochondrial membranes, and/or material that is present in mitochondrial membranes can be used as a detection system to optically detect the presence and/or absence of various materials.

24 Claims, 5 Drawing Sheets

METHODS AND COMPOSITIONS FOR SENSORS

CLAIM FOR PRIORITY

This application is the U.S. national phase entry under 35 U.S.C. §371 of PCT/US2011/065808, filed Dec. 19, 2011, the entire disclosure of which is hereby incorporated by reference herein.

TECHNICAL FIELD

Some embodiments herein generally relate to compositions, manufactures, and methods for sensing compositions in air and/or other fluids.

BACKGROUND

A variety of devices and methods exist for sensing contaminants in air and other fluids. Traditionally, such devices, including for example, smoke detectors or various gas detectors, focus on addressing a very particular set of possible contaminants.

SUMMARY

In some embodiments, methods and compositions are provided for sensing of air or other fluid quality.

In some embodiments, a sensing particle is provided. The particle can include an isolated, de-energized, mitochondrial particle. In some embodiments, the mitochondrial particle can have a diameter of about 0.01 micrometer to about 10 micrometer.

In some embodiments, an air quality sensor is provided and can include at least one sensing particle including an isolated, de-energized, mitochondrial particle, and a semi-transparent or a transparent surface. In some embodiments, the at least one sensing particle is attached to the surface.

In some embodiments, an air quality measurement device is provided. The device can include an air intake port and a first air emission output configured to direct a quantity of air onto a location configured to receive an air quality sensor. In some embodiments, the air intake port is in fluid communication with the first air emission output. In some embodiments, a first radiation source configured to emit radiation having a substantially uniform first wavelength onto the location is provided and a detector configured to measure a wavelength of radiation, an intensity of radiation, or the lifetime of the radiation, or all three emitted from the location is provided.

In some embodiments, a method of sensing air quality is provided. The method can include providing a first isolated, de-energized, mitochondrial membrane, contacting the mitochondrial membrane with a quantity of air to be tested, applying a first amount of radiation to the mitochondrial membrane, and measuring an optical characteristic of the mitochondrial membrane and/or radiation emitted by the mitochondrial membrane.

In some embodiments, a method of making an air quality-sensing particle is provided. The method can include providing a sample containing at least one mitochondria, and extruding the mitochondria through at least one pore such that a mitochondrial particle is formed that has a diameter of about 0.5 to about 16 micrometers.

In some embodiments, a particle derived from mitochondria is provided. In some embodiments, a fluorescence signature is used to determine the identity and/or concentration of a known compound. In some embodiments, the fluorescence signature of an unknown compound is collected and used for identification of the compound by comparison of the signature with the signatures of one or more known compounds. In some embodiments, manufactures for sensing air quality are provided, for example air quality sensing devices, and air quality measurement devices. Such methods and devices can be used, for example, to detect harmful pollutants in a factory, or detect a bioterrorism threat in a population center.

DETAILED DESCRIPTION

Figure 1:
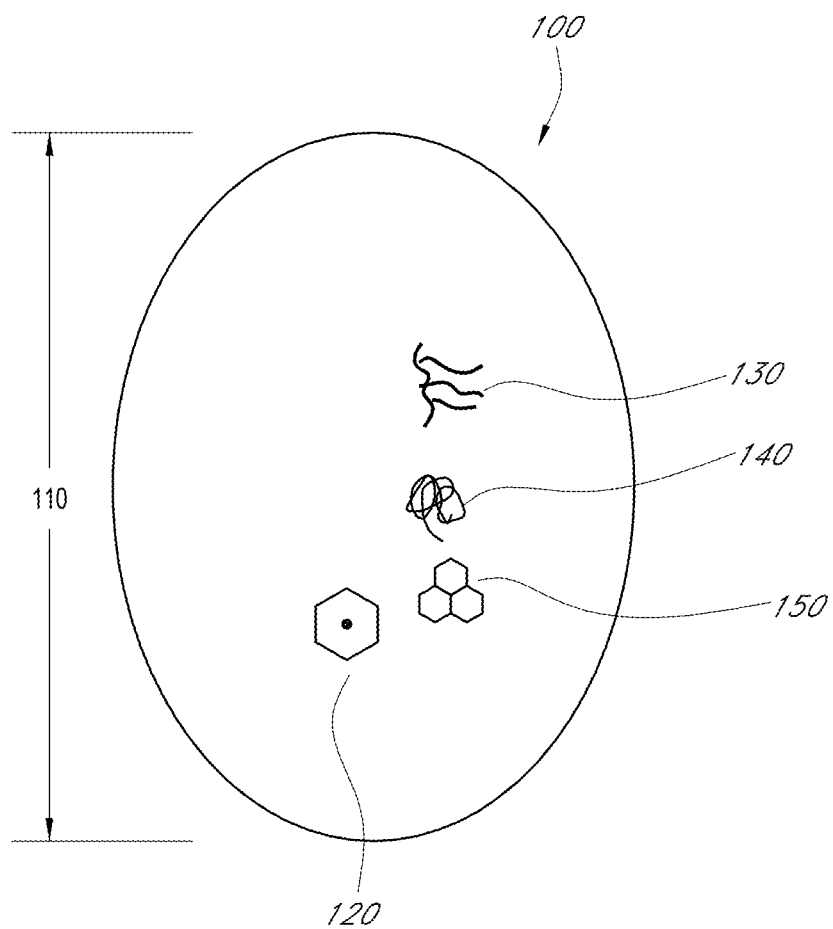
FIG. 1 is a drawing depicting some embodiments of a sensing particle.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Provided herein are embodiments that can be employed in the detection of materials or contaminants in air and other fluids. In some embodiments, mitochondrial membranes, constituents thereof, and/or derivatives thereof can be used as, or as part of, a detection system (in the form of sensing particles or sensing membranes). In some embodiments, the sensing particle and/or constituents from the mitochondrial membrane can interact with contaminants or other ingredients in the air or fluid and result in a change in at least one optical property of the system. This optical signature and/or change (or a combination of such changes) can be used to identify contaminants or impurities in the air or fluid.

FIG. 1 depicts some embodiments of a sensing particle 100. In some embodiments the sensing particle 100 can be a mitochondrion, can be part of a mitochondrion, can be derived from a mitochondrion, or can contain components that are also found in a mitochondrion. In some embodiments, the sensing particle includes a portion of a mitochondrion. In some embodiments, the sensing particle includes an entire mitochondrion. In some embodiments, the sensing particle has been de-energized and/or isolated.

In some embodiments, the sensing particle includes a lipid 130, such as those native to mitochondria. In some embodiments, the sensing particle includes a protein 140, such as those native to mitochondria. In some embodiments, the sensing particle includes a carbohydrate 150, such as those native to mitochondria. In some embodiments, the sensing particle includes a cholesterol moiety, such as those native to mitochondria.

In some embodiments, the sensing particle has a diameter 110 of about 0.05 micrometers to about 16 micrometers, e.g., a diameter of about 0.01, 0.02, 0.03, 0.04, 0.05, 0.06, 0.07, 0.08, 0.09, 0.10, 0.15, 0.2, 0.3, 0.4, 0.5, 0.6, 0.7, 0.8, 0.9, 1, 2, 3, 4, 5, 6, 7, 8, 9, 10, 11, 12, 13, 14, 15, or 16 micrometers, including any range between any two of the preceding values. In some embodiments, the sensing particle has a diameter 110 of about 0.01 micrometer to about 10 micrometers. In some embodiments, the sensing particle has a diameter of about 0.05 micrometer to about 2 micrometers. In some embodiments, the sensing particle has a diameter of about 0.1 micrometer to about 0.4 micrometers.

In some embodiments, the sensing particle includes at least a portion of a first mitochondrion and at least a portion of a second (or more) mitochondrion. In some embodiments, the sensing particle includes at least a portion of three or more mitochondria.

In some embodiments, the sensing particle is at least partially de-energized. In some embodiments, the sensing particle is completely de-energized. In some embodiments, the sensing particle is substantially de-energized. In some embodiments, the sensing particle has been de-energized by extruding a mitochondrion through at least one pore to form the particle.

In some embodiments, the sensing particle includes one or more heme groups 120. In some embodiments at least 80% of the heme groups in the sensing particle include an iron atom in the ferric state, e.g., 80, 85, 90, 95, 99, 99.9% or more of the heme groups are in the ferric state.

In some embodiments, the sensing particle has no significant proton gradient across a membrane of the sensing particle. In some embodiments, the sensing particle has no intact inner membrane.

As will be appreciated by one of skill in the art, given the present disclosure, compounds that are present in the mitochodrial membrane can be useful as a sensor as the membrane is protein-rich and contains many cytochromes with spectrally rich signatures. In some embodiments, these signatures have one or more intrinsic fluorescence peaks. In some embodiments, other cell based membranes can be used. In some embodiments, the outer membrane of a biological cell can be used.

In some embodiments, the lipid interacts with a pollutant or other compound, thereby causing the lipid to undergo a conformational change that causes an optical or spectral change in the particle (e.g., via the lipid or the lipid's interaction with the particle). In some embodiments, the fluorescent properties of the particle changes. In some embodiments, an absorbance property of the particle changes.

In some embodiments, the protein 140 interacts with a pollutant or other compound, thereby causing the protein to undergo a conformational change that causes a change in at least one fluorescence aspect of the particle (e.g., via the protein or the protein's interaction with the particle).

In some embodiments, the carbohydrate 150 interacts with a pollutant or other compound, thereby causing the carbohydrate to undergo a conformational change that causes a change in at least one fluorescence aspect of the particle (e.g., via the carbohydrate or the carbohydrate's interaction with the particle).

In some embodiments, additional compounds are added to the sensing particle. For example, chlorophyll can be added to the mitochondrial particle, thereby permitting interactions to occur between chlorophyll and various compounds, for example pollutants or contaminants.

Figure 2:
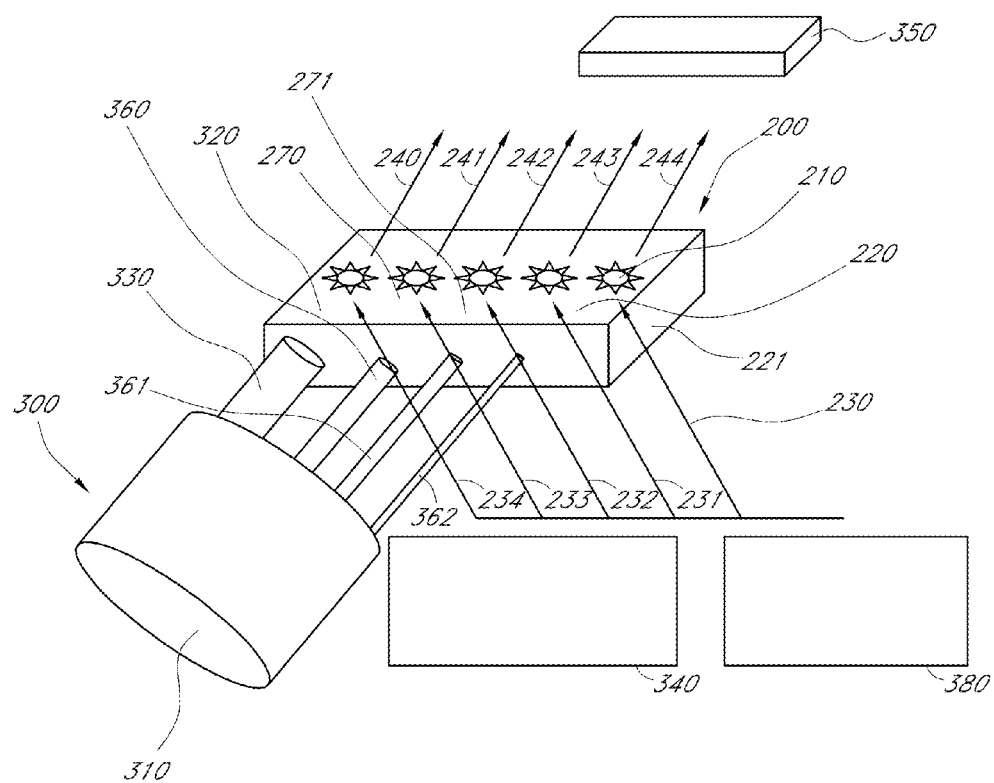
FIG. 2 is a drawing depicting some embodiments of an air quality measurement device and air quality sensor.

In some embodiments, an air quality sensor 200 is provided (FIG. 2). In some embodiments, the air quality sensor includes at least one sensing particle 210. In some embodiments, the air quality sensor includes at least one surface 220 of a support 221. In some embodiments, the surface 220 of a support 221 is semi-transparent or transparent. In some embodiments, the surface 220 and/or support 221 is not transparent. In some embodiments, the support 221 and/or surface 220 allows for visible light to pass through it. In some embodiments, the support 221 and/or surface 220 allows light having a wavelength from 200 to 700 to pass through it. In some embodiments, the support 221 and/or surface 220 acts as a filter to select a wavelength of light passing from a first side to a second side, from the second side to the first side, or passing both directions. In some embodiments, the sensor permits the transmission of radiation of at least one wavelength, for example to excite the at least one sensing particle and observe fluorescence or other optical property of the at least one sensing particle.

In some embodiments, the surface 220 is configured to permit the transmission of radiation 230. In some embodiments, the radiation is of a first wavelength 230. In some embodiments, the radiation is also of a second wavelength 231. In some embodiments, the radiation is also of a third wavelength 232. In some embodiments, the radiation is also of a fourth wavelength 233. In some embodiments, the radiation is also of a fifth wavelength 234. In some embodiments, there is radiation of at least one wavelength in addition to the fifth wavelength. In some embodiments, the support and/or surface is transparent to any and/or all of the wavelengths being used to excite or monitor the sensing particles.

In some embodiments, the surface 220 includes a sponge-like material, for example a transparent or semi-transparent polymer. In some embodiments, the surface includes a foam. In some embodiments, the sponge-like material allows the surface to retain the sensing particle 210. In some embodiments, the surface includes a polymer. In some embodiments, the sponge-like material and/or polymer provides more surface area for the sensing particle 210.

In some embodiments, the air quality sensor includes at least 2 sensing particles, e.g., 10, 50, 100, 200, 500, 1,000, 10,000, 100,000, 1,000,000, 10,000,000, or 100,000,000 sensing particles, including any range above any of the preceding values, and any range between any two of the preceding values.

In some embodiments, the sensing particle is immobilized on the surface. In some embodiments, the at least one sensing particle is attached to the surface. In some embodiments, the at least one sensing particle contacts, but is not attached to the surface. In some embodiments, at least a first sensing particle is attached to the surface, while at least a second sensing particle contacts the surface, but is not attached to the surface. In some embodiments the sensing particle 210 is embedded in the surface 220. For example, when the surface includes a foam, the sensing particle can be embedded in the foam. In some embodiments, the sensing particle is covalently cross-linked to the surface. In some embodiments, the cross-linking is non-specific. In some embodiments, the cross-linking includes aldehydes, or cross-linkers similar to aldehydes. In some embodiments, there is sufficient cross-linking to attach the at least one particle to the surface, without cross-linking substantially all of the molecules of the particle to the surface or to each other. In some embodiments, substantially uniform numbers of cross-linkers between each sensing particle and the surface is achieved. In some embodiments, this can reduce batch-to-batch variation. In some embodiments, the sensing particle 210 is attached via a sulfur atom, such as a disulfide bond. In some embodiments, the sensing particle 210 is attached via a hydrophobic interaction with the surface. In some embodiments, the surface 220 can include chemical moieties or modifications (such as hydrophobic chains, sulfur groups, gold, etc) so as to allow covalent or non-covalent associations with the sensing particle.

In some embodiments, the surface is configured to permit the transmission of radiation having wavelengths of about 200 nanometers to about 600 nanometers (e.g., 230, 231, 232, and 234). In some embodiments the radiation of has a wavelength of 200, 220, 240, 260, 280, 300, 320, 340, 360, 380, 400, 420, 440, 460, 480, 500, 520, 540, 560, 580, 600, 620, or 640 nm, including any range below any of the preceding values, any range above any of the preceding values, and any range between any two of the preceding values. In some embodiments, the process can involve scanning across wavelengths from 200 to 640 nm at 1-5 nm increments.

In some embodiments, the support 221 can have a flat surface 220. In some embodiments, the support 221 can have a curved surface. In some embodiments, the surface can be smooth. In some embodiments, the surface can be rough. In some embodiments, the support can be one or more particles and/or beads, and the surface 220 can be effectively distributed over numerous particles.

In some embodiments, each sensor 200 can have a different type of sensing particle 210 associated with it. In some embodiments, each sensor can have a 1, 2, 3, 4, 5, 6, 7, 8, 9, 10, 20, 30, 50, 100, 200, or 500 types of sensing particles associated with it, including any range above any one of the preceding values and any range between any two of the preceding values. In some embodiments, a single (and/or consistent) type of sensing particle 210 is used on each sensor 200. In some embodiments, a mixture of sensing particles 210 is used on each sensor 200. In some embodiments, the mixture is based upon the items (e.g., contaminants) that could be detected in a sample to be tested. In some embodiments, the mixture is based upon items that are likely to be present in a sample to be tested. In some embodiments, the mixture is based upon items that one is concerned about or wishes to detect.

In some embodiments, an air quality measurement device 300 is provided (FIG. 2). In some embodiments, the air quality measurement device includes at least one air emission output 330 configured to direct air onto an air quality sensor 200 or a space configured to receive an air quality sensor. In some embodiments, the air quality measurement device 300 includes a first radiation source 340 configured to emit radiation onto the air quality sensor 200 or a space configured to receive an air quality sensor 200. In some embodiments, the air quality measurement device includes one or more detectors 350 configured to measure at least one characteristic of radiation emitted by the sensor.

In some embodiments, the detector 350 and the radiation source 340 are on a same side of the air quality sensor (e.g., so that radiation emitted from the radiation source 340 hits the sensor 200 and then emitted radiation then returns back the way the radiation initially came to the detector 350). In some embodiments, the detector 350 and the radiation source 340 are on opposite sides of the air quality sensor (e.g., so that radiation emitted from the radiation source 340 hits the sensor 200 and then emitted radiation is then emitted on the opposite side, passes through (or by) the support 221 and then to the detector 350). In this arrangement, aspects such as radiation absorption can also be examined.

In some embodiments, the device 300 includes an air intake port 310. In some embodiments, the device includes one or more air emission outputs (e.g., 330, 360, 361, and 362) configured to direct a quantity of air onto a location 320 of an air quality sensor 200. In some embodiments, the air intake port 310 is in fluid communication with the first air emission output 330.

In some embodiments, the device 300 includes a second air emission output 360 configured to direct a quantity of air onto a second location 370. In some embodiments, the device includes a third air emission output 361 configured to direct a quantity of air onto a third location 371. In some embodiments, the device 300 includes a fourth air emission output 362 configured to direct a quantity of air onto a fourth location 372.

In some embodiments, the first, second, third, and/or fourth air emission outputs (330, 360, 361, and 362) are of different sizes, for example different diameters, thereby emitting different quantities of air on the first, second, third, and/or fourth locations (320, 370, 371, and/or 372). In some embodiments, the diameter of an air emission output is less than 1, 2, 3, 4, 5, 10, 20, 50, 100, 1000, 10,000, 100,000, 1,000,000, or 10,000,000 micrometers, including any range above any of the preceding values and any range between any two of the preceding values. In some embodiments, the range of sizes can allow for varying amounts of air and/or fluid samples to be moved across the sensor at a time. In some embodiments, the movement of air or other fluid across the sensor can be done serially. In some embodiments, the movement of air or other fluids can be done at overlapping times and/or simultaneously.

In some embodiments, the device 300 can include one or more radiation sources 340, 350. In some embodiments, the radiation source 340 is configured to emit radiation having a substantially uniform first wavelength onto a space configured to receive the sensor 200. In some embodiments, the radiation source 340 and/or other radiation directing and/or filtering systems (such as lenses, minors, and/or filters) can direct some or all of the radiation to one or more of the locations 320, 360, 361, and 362, so that the optical excitation and/or emission will occur, in part, (or in all) from a location that is experiencing exposure to the sample volume of air or fluid.

In some embodiments, the radiation source 340 emits a broad spectrum of radiation. In some embodiments, the radiation source 340 and/or other radiation directing and/or filtering systems (such as lenses, minors, and/or filters) can selectively direct various aspects of radiation to one or more of the locations 320, 360, 361, and 362, so that the optical excitation and emission will occur in part (or in all) from a location that is experiencing exposure to the sample volume of air. In some embodiments, this allows for various optical aspects that are occurring in the sensing particles to be monitored simultaneously. In some embodiments, different wavelengths, intensities, durations, etc., of radiation are each provided to irradiate one or more of the locations 320, 370, 371, and 372, so that one or more resulting optical characteristic can be monitored.

In some embodiments, the same type of sensing particle 210 can be employed at each location. In some embodiments, the sensing particle 210 can be different at each location. In some embodiments, a collection of types of sensing particles can be paired with appropriate irradiation parameters so that the type of excitation aspect (e.g., intensity, wavelength, duration) can be paired with an appropriate sensing particle to detect a specific contaminant.

In some embodiments, the device 300 includes at least one detector 350 configured to measure a wavelength of radiation, an intensity of radiation, the lifetime of radiation, or any combination thereof from the location. In some embodiments, the device 300 includes more than one detector, so that various optical characteristics (e.g., wavelength of radiation, an intensity of radiation, absorption characteristic, FRET, or the lifetime of the radiation) can be measured simultaneously or concurrently. In some embodiments, the device includes an optical input to collect radiation coming from the sensing particle 210. In some embodiments, the optical input can be split, so as to divide the radiation for separate types of analysis.

In some embodiments, the air quality measurement device 300 includes at least one air intake port 310. In some embodiments, there is a fan/vacuum system to bring the air into the port at a set rate. In some embodiments, the air is taken and/or piped from a screening area, such as a security system for monitoring people or bags.

In some embodiments, each radiation source is configured to direct radiation onto all of the locations where air is deposited by an air emission output. In some embodiments, each radiation source is configured to emit radiation having wavelengths 230 of about 200 nanometers to about 600 nanometers. In some embodiments the radiation has a wavelength of 200 nm to 640 nm, e.g., 200, 220, 240, 260, 280, 300, 320, 340, 360, 380, 400, 420, 440, 460, 480, 500, 520, 540, 560, 580, 600, 620, or 640 nm, including any range between any two of the preceding values.

In some embodiments, the air quality measurement device 300 includes at least one air quality sensor 200, wherein the sensor includes a sensing particle attached to a support. In some embodiments, the air quality measurement device 300 includes a space configured to receive an air quality sensor. For example, a space that is configured to position the air quality sensor, while allowing air or another fluid to be directed to the space, allowing radiation to irradiate the space, and allowing emitted radiation to be collected and/or analyzed.

In some embodiments, the air intake port 310 produces an air stream at a set flow rate that is then directed to each air emission output (for example, the first and second air emission output; the first, second, and third air emission output; the first, second, third and fourth air emission output; or the first, second, third, fourth and at least one additional air emission output), to obtain a real-time dose response. In some embodiments, a difference in size between two of the emission outputs separates the air to produce a dose response. Thus, in some embodiments, the device 300 is capable of generating simultaneously produced dose response curves, as differing amounts of air samples can be tested at the same time.

In some embodiments, the air intake port 310, or a chamber in fluid communication with the air intake port, directs an air stream to each air emission output so that the air stream directed to each emission output has a different pressure, thereby producing a dose response.

In some embodiments, the air intake port 310, or a chamber in fluid communication with the air intake port, directs the airstream to each air emission output in such a way as to achieve a different duration of exposure, thereby producing a dose response. In some embodiments, the dose response can vary over several orders of magnitude.

In some embodiments, the device is configured to have a control location onto which no air and/or fluid is deposited. In some embodiments, the control location receives air that is known to be free of contaminants. In some embodiments, the control location receives air that has been filtered. In some embodiments, the control location receives air that that is known to be free of the contaminant(s) to be searched for. In some embodiments, the control location receives air that contains a known amount of a contaminant.

In some embodiments, the air quality measurement device 300 is configured to provide and/or allow for parallel fluorometery. In some embodiments, the detector 350 collects radiation emissions of various excitation wavelengths, such as about 200 nm to about 700 nm. In some embodiments, the device measures time-resolution for each wavelength collected, thereby permitting the calculation of half-lives. In some embodiments, the device determines half-lives. In some embodiments, the device scans across a range of excitation wavelengths and measures the emission intensity and lifetimes across a range of wavelengths. In some embodiments, the device obtains measurements of fluorescence intensity and half-lives scanned across a range of excitation and emission wavelengths.

In some embodiments, the device produces real time measurements in 1, 2, 3, 4, 5, 6, 7, 8, 9 or ten dimensions: fluorescence intensity x, excitation wavelength x, emission wavelength x, dose x, and time; and fluorescence lifetime x, excitation wavelength x, emission wavelength x, dose x, and time. In some embodiments, the device combines the real time measurements computationally to produce a dose-dependent fluorescence signature. In some embodiments, devices and components for this are also contemplated.

As noted above, in some embodiments, the molecular interactions between the one or more sensing particle and different compounds, for example pollutants, cause the fluorescence signature of the sensing particle to change. In some embodiments, the device calculates or determines the change in fluorescence signature. In some embodiments, this is done by comparison of a sample fluorescence signature with a control fluorescence signature. In some embodiments, the control fluorescence signature is from a database and/or computer-readable medium. In some embodiments, the control fluorescence signature is obtained simultaneously and/or concurrently with the sample. In some embodiments, the control fluorescence signature is automatically subtracted from the fluorescence signature, in order to create the fluorescence signature of the sample. In some embodiments this change in fluorescence signature (or the final fluorescence signature) is then compared to various fluorescence signatures of known compounds. In some embodiments, when a match (and/or partial match) is identified, one has then identified the contaminant in the air and/or fluid. In some embodiments, a match need not be made, but instead any change in the fluorescence signature beyond the baseline control level can be indicative of the presence of a contaminant. In some embodiments, the device, or a computer (and/or a computer-readable medium) associated with the device, is programmed to perform and/or store code for any of the methods and/or processes described herein. For example, in some embodiments, the computer and/or computer-readable medium compares changes caused by known pollutants to determine type and dose of compound in a sample volume. In some embodiments, the device (and/or computer-readable medium) detects and/or identifies changes caused by at least one unknown compound. In some embodiments, the device is operationally connected to a database, and stores information of known and/or unknown contaminants and/or compounds and/or controls on a computer-readable medium for possible future identification. In some embodiments, the device and/or computer-readable medium is configured to make comparisons in order to determine concentrations and/or changes in concentrations of the compounds.

In some embodiments, the device and/or code on the computer-readable medium is self-learning. In some embodiments, a data set is obtained, and the self-learning function of the device provides a very sensitive and robust detection. In some embodiments, once an initially unknown compound in a sample of air is identified by subsequent testing (e.g., running various known contaminants until a known contaminant produces a fluorescence signature that is in part or in whole the same as the fluorescence signature of the sample), the results are added to the database and/or computer-readable medium so that next time a comparison can be made with that signature.

In some embodiments, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented using any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 3A:
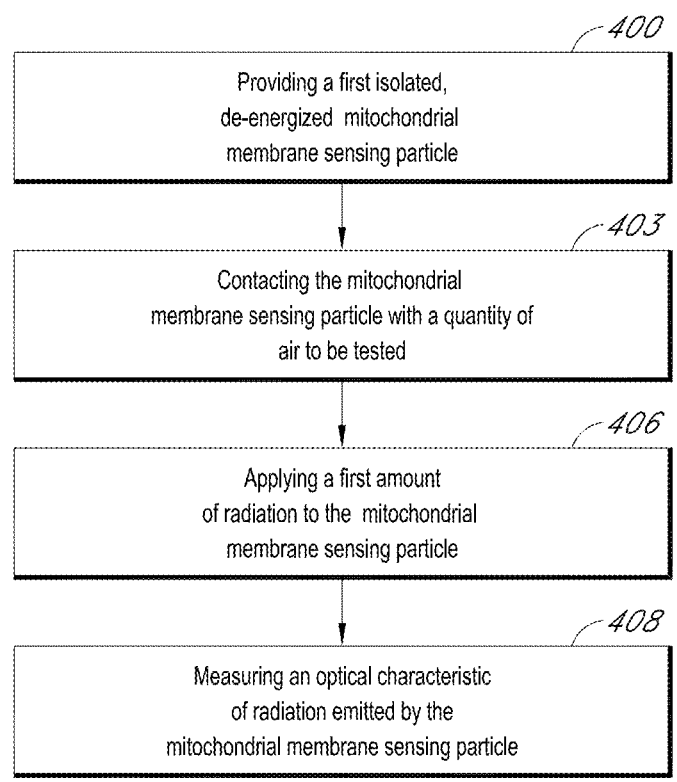
FIG. 3A is a flow chart depicting some embodiments of a method of sensing air quality.

In some embodiments, a method of sensing air quality is provided (FIG. 3A). In some embodiments, the method includes providing a first sensing particle (block 400). In some embodiments, the method includes contacting a sensing particle with a quantity of air to be tested (block 403). In some embodiments, the method includes applying a first amount of radiation to the sensing particle (block 406). In some embodiments, the method includes measuring an optical characteristic of radiation emitted by the sensing particle (block 408).

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 3B:
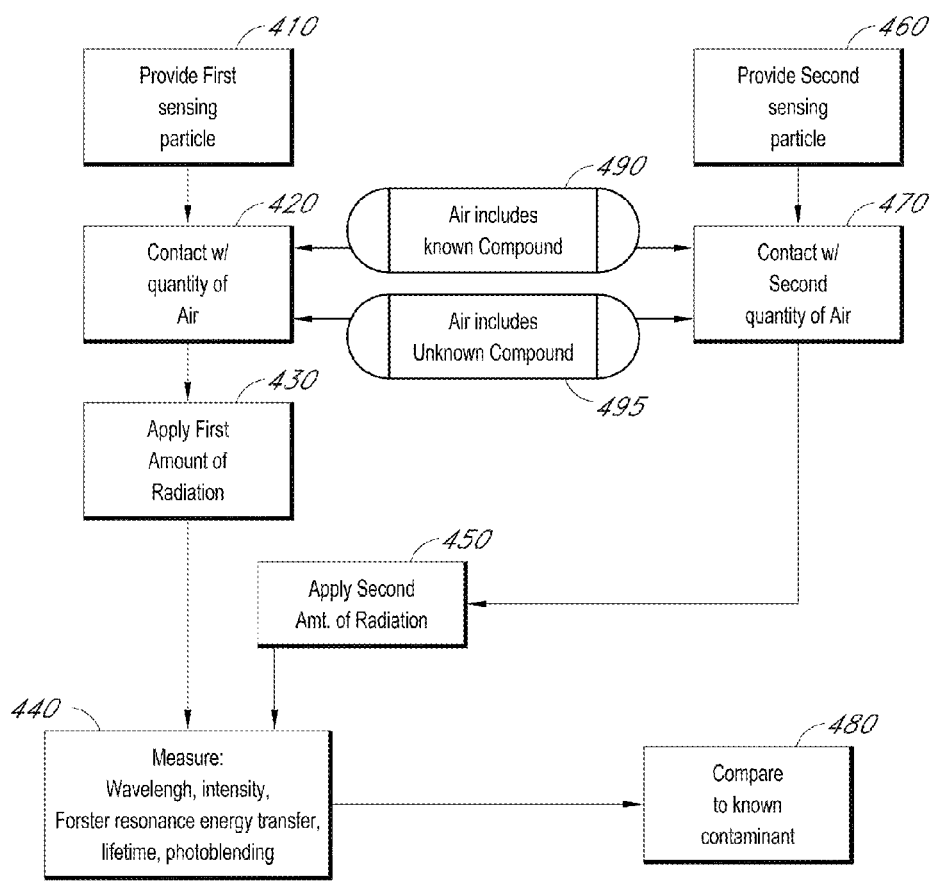
FIG. 3B is a flow chart depicting some embodiments of a method of sensing air quality.

The various devices and components provided herein can be employed for a variety of methods. In some embodiments, the method of comparing and/or identifying contaminants includes providing a first sensing particle (block 410) (FIG. 3B). In some embodiments, the method includes contacting the sensing particle with a quantity of air to be tested (block 420). In some embodiments, the method includes applying a first amount of radiation to the sensing particle (block 430). In some embodiments, the method includes measuring an optical characteristic of radiation emitted by the sensing particle (block 440). In some embodiments, the method includes measuring an optical characteristic of the radiation emitted by the sensing particle. In some embodiments, the optical characteristic or "signature" of the radiation emitted from the sensing particle when exposed to the sample is then used in any number of ways to identify if a contaminant is present in the sample. The method can also, in some embodiments, identify what type, how much, etc., of the contaminant is present. In some embodiments, this can be achieved by observing the fluorescence signature produced, the change in fluorescence signature produced (in comparison to a control sample) and/or the comparison of the fluorescence signature (and/or its change) to one or more fluorescence signatures of various known and/or control samples.

In some embodiments, the optical characteristic includes measuring at least one of: a wavelength of the emitted radiation, an intensity of the emitted radiation, Förster resonance energy transfer, photobleaching, wavelength or amount of light absorbed, or lifetime of the fluorescence. In some embodiments, the optical characteristic includes measuring the Stokes shift and/or quantum yield. In some embodiments, the optical characteristic includes monitoring two-photon absorption, which leads to shorter wavelength emission. In some embodiments, the optical characteristic includes fluorescence fluctuations, fluorescence recovery after photobleaching (FRAP), and/or fluorescence quenching.

In some embodiments, the method includes applying a second amount of radiation to the sensing particle, where the second amount of radiation has a substantially different wavelength than the first amount of radiation (block 450). In some embodiments, the method includes providing a second isolated, sensing particle (block 460). In some embodiments, the method includes contacting the second sensing particle with a second quantity of air to be tested (block 470). In some embodiments, the method includes applying a second amount of radiation to the second sensing particle wherein the second amount of radiation has a substantially different wavelength than the first amount of radiation. In some embodiments, the method includes comparing the optical characteristic of radiation emitted by the second sensing particle to an optical characteristic of a known contaminant (block 480). In some embodiments, the quantity of air to be tested includes at least one known compound (block 490). In some embodiments, the quantity of air to be tested includes at least one unknown compound (block 495).

In some embodiments, data are collected for at least two different quantities of air in order to provide a real-time dose response curve. For example, for each wavelength set collected (e.g. a 3-D scan of excitation and emission wavelengths), a dose response curve can be established for both fluorescence intensity and for fluorescence lifetime. In some embodiments, the data set is collected repeatedly, with measurements taken at regular intervals. The intervals can be as desired and can be application specific, some possible times are every 0.1 s, 0.2 s, 0.3 s, 0.4 s, 0.5 s, 0.6 s, 0.7 s, 0.8 s, 0.9 s, 1 s, 2 s, 3 s, 4 s, 5 s, 6 s, 7 s, 8 s, 9 s, 10 s, 20 s, 30 s, 40 s, or 50 seconds, or one minute, two minutes, three minutes, four minutes, or five minutes, including any range below any of the preceding values, any range above any of the preceding values and any range between any two of the preceding values.

In some embodiments, the method includes applying a second amount of radiation to the mitochondrial membrane, wherein the second amount of radiation has a substantially different wavelength than the first amount of radiation. In some embodiments, the second amount of radiation has a wavelength of about 200 nm to about 640 nm, e.g., 200, 220, 240, 260, 280, 300, 320, 340, 360, 380, 400, 420, 440, 460, 480, 500, 520, 540, 560, 580, 600, 620, or 640 nm, including any range between any two of the preceding values.

In some embodiments, at least a first amount of radiation is applied to a third, fourth, fifth, sixth, seventh, eighth, ninth, tenth, or additional sensing particle. In some embodiments, at least a second amount of radiation is applied to the third, fourth, fifth, sixth, seventh, eighth, ninth, tenth, or additional sensing particle.

In some embodiments, the optical characteristic of radiation emitted by the sensing particle is compared to an optical characteristic of a known contaminant. In some embodiments, the optical characteristic is of the first sensing particle. In some embodiments, the optical characteristic is of the second sensing particle. In some embodiments, the optical characteristic is of the first and second sensing particles.

In some embodiments, the quantity of air to be tested includes at least one unknown compound. In some embodiments, at least one optical characteristic of the at least one unknown compound is stored in a database, for example on a computer-readable medium. In some embodiments, the at least one optical characteristic of the at least one unknown compound is stored in a database for future identification. In some embodiments, the identity of the unknown compound is learned, or a functional property of the unknown compound is obtained, and the database is updated with this identity or functional property, thereby permitting the future identification of the previously unknown compound.

In some embodiments, at least one reference signature is provided for a particular contaminant or amount of a contaminant. For example, in some embodiments, at least one optical characteristic of a known compound can be provided and/or determined. In some embodiments, a reference signature can have a number of fluorescence peaks and troughs, each of which has an associated fluorescence half-life (or other optical characteristic). In some embodiments, a control sensor can establish, and/or retain this baseline signature. Thus, in some embodiments, data from the other channels can be compared to the reference signature and differences due to molecular interactions with the sensors can be determined with great sensitivity. In some embodiments, the reference signature can be stored on a computer-readable medium. In some embodiments, the reference signature is a positive control. In some embodiments, a computer or other device can compare one or more reference signatures to the fluorescence signature generated by the sample (via the sensing particles), and identify peaks in common between the two. In some embodiments, when a sample signature has a sufficient similarity to a reference signature, a match can be declared. In some embodiments, a sample signature will have at least all of the peaks of a reference signature, although, in some embodiments, it can have more peaks.

In some embodiments, when a compound binds to a molecule in the sensing particle and causes a conformation change that alters the fluorescence (or other optical properties) of the particle, that compound will be associated with a particular signature of optical characteristics. For example, the signature of optical characteristics can be manifested as changes any one or more of the following: the peaks/troughs intensities and half-lives, changes in Stokes shifts, new peaks/troughs arising, and/or changes in any FRET present in the system. In some embodiments, the signature change will be unique to the compound and can be described by a dose response curve. In some embodiments, the compound will have a unique time signature. In some embodiments, overall changes in the signature, as well as differential changes (e.g. slope of the time-response and dose-response curves at different wavelengths) can be used to describe the interaction of a particular compound with a sensing particle. In some embodiments, any of the above can be used for the creation of a sample's fluorescence signature and/or a reference's fluorescence signature.

In some embodiments, at least two different quantities of air to be tested are applied to at least two different sensing particles, and a dose response curve can be calculated. In some embodiments, a dose-response curve for a known quantity of compound is compared to a dose response curve from the quantity of air that was tested, thereby determining the concentration of the compound in the quantity of air that was tested. In some embodiments, the derivative, or second-derivative of this curve is informative. In some embodiments, multiple dose response curves (eg intensity and lifetime curves), and their derivatives are generated to provide the signature. Thus, in some embodiments, the identity and/or concentration of the species of compound—for example a pollutant—being measured by the sensing particle can be determined through signature fitting.

In some embodiments, parallel fluorometery can be performed. In some embodiments, the radiation emissions are measured simultaneously. In some embodiments, time-resolution data for each wavelength collected is measured, thereby permitting the calculation of half-lives. In some embodiments, a range of excitation wavelengths is scanned, and the emission intensity and lifetimes across a range of wavelengths is measured. In some embodiments, the measurements of fluorescence intensity and half-lives scanned across a range of excitation and emission wavelengths are obtained.

In some embodiments, the real time measurements in 1, 2, 3, 4, 5, 6, 7, 8, 9, 10 or more dimensions are produced, e.g.: fluorescence intensity x, excitation wavelength x, emission wavelength x, dose x, time, for a first amount of radiation; and fluorescence lifetime x, excitation wavelength x, emission wavelength x, dose x, and time for a second amount of radiation. In some embodiments, the real-time measurements are combined computationally to produce a dose-dependent fluorescence signature. In some embodiments, at least one molecular interaction between at least one contaminant and at least one component of the sensing particle cause the fluorescence signature to change. In some embodiments, the change in fluorescence signature is calculated and compared to changes caused by known compounds to determine type and dose of the contaminant. In some embodiments, changes caused by the at least one unknown compounds are also detected. In some embodiments the changes are added to a database. In some embodiments, the changes caused by the at least one unknown compound are used for future identification.

In some embodiments, the measurements are initially calibrated with known concentrations of known compounds to establish these signatures. Since each different contaminant will interact with the molecular makeup of the sensor in a different way, the dataset can be robust enough to determine a unique signature for many different molecules and combinations thereof.

In some embodiments, an air sample is monitored, and an "unknown signature" is identified which does not correspond to a signature in a known data set. In some embodiments, the unknown signature triggers an alert for follow-up, for example using the techniques of GC-MS or GC-FTIR. The later identification of the compound's composition, or of a functional property of the compound can be entered into a database, thereby permitting the identification of that compound in the future. In some embodiments, the data set is entered onto a computer-readable medium.

Figure 4:
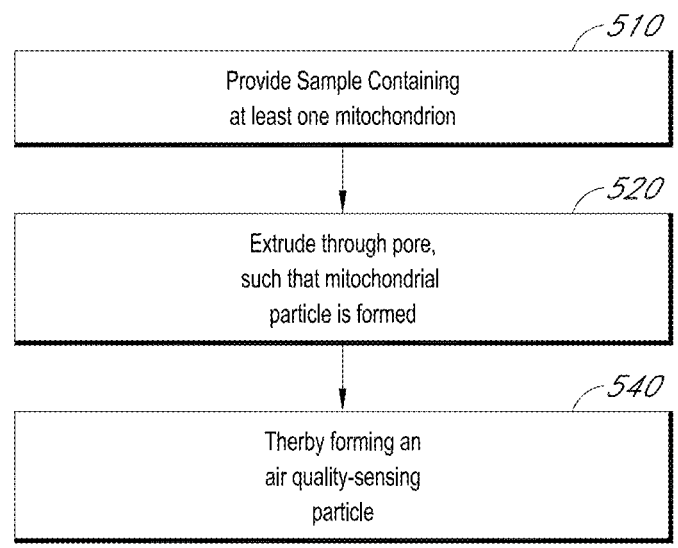
FIG. 4 is a flow chart depicting some embodiments of a method of making a sensing particle.

In some embodiments, a method of making an air quality-sensing particle is provided as outlined in FIG. 4. In some embodiments, the method includes providing a sample containing at least one mitochondrion (or a membrane thereof) (block 510). In some embodiments, the method includes extruding the mitochondrion through at least one pore such that a sensing particle is formed 520, thereby making an air quality-sensing particle 540.

Mitochondria are available from many sources, for example offal from abattoirs like liver, or extracts thereof. In some embodiments, the mitochondria are isolated using standard techniques to rupture the cell, remove the debris and larger organelles. In some embodiments, the mitochondria are purified using standard techniques. In some embodiments, purified mitochondria are used to prepare mitochondrial particles by extrusion of the mitochondria through at least one pore of a set size, thereby homogenizing the mitochondria. In some embodiments, one does not use a mitochondrion, but instead collects the proteins, lipids, and other molecules present in a mitochondrial membrane and uses them to create an artificial membrane. Thus, the sensing particle need not be originally from or in the form of a mitochondrion in all embodiments. In some embodiments, the pore has a diameter of about 0.5 micrometers to 16 micrometers, e.g., 0.5, 1, 2, 3, 4, 5, 6, 7, 8, 9, 10, 11, 12, 13, 14, 15, or 16 microns, or ranges between any two of these values.

In some embodiments, extruding the mitochondria through the at least one pore de-energizes the sensing particle. For example, extruding the mitochondria through the at least one pore can disrupt mitochondrial inner membranes, thereby eliminating all substantial proton gradients across those inner membranes, thereby de-energizing the sensing particles.

In some embodiments, the extrusion de-energizes the mitochondrial particle so as to provide a steady baseline and/or consistency across various sensing particles. In some embodiments, the sensing particle is partially de-energized. In some embodiments, the sensing particle is fully de-energized. In some embodiments, de-energizing is performed, at least in part by contacting the mitochondria or sensing particle with a decoupling agent, for example FCCP.

In some embodiments, the de-energizing is performed, at least in part, by contacting the mitochondria or sensing particle with a reducing agent, for example a metal.

Additional Alternative Embodiments

In some embodiments, a low-cost air quality monitoring can be provided. In some embodiments, a portable solution for air quality monitoring is provided. In some embodiments, provided herein are low-cost, portable, air quality monitoring systems, which offer adequate discriminatory ability amongst different air contaminants.

In some embodiments, particles derived from mitochondria offer an extraordinary range of both spectrally active material, as well as binding partners for many known pollutants. In some embodiments, fully energized mitochondria are impractical due to their instability and thus changing baseline, so de-energized mitochondrial particles are used instead.

In some embodiments, a data set of signatures (e.g., control and/or reference and/or sample signatures) can further be enhanced by measuring the fluorescence peaks and troughs as they change with different doses of molecules interacting with the sample. In some embodiments, unique molecular interaction can cause unique signatures not only in the peaks and troughs they alter, but will be described by a unique dose response. Thus, in some embodiments, a dose response signature is obtained, both for reference signatures and for sample signatures, and comparisons of the dose response curves can be made. In some embodiments, this determination will afford the discrimination of unique molecular interactions in complex mixtures and determine not only their species, but, optionally, their concentrations as well.

EXAMPLE 1

Preparation of an Air Quality Sensor

The present example outlines how to prepare an air quality sensor. A collection of cells is gathered and the mitochondria from the cells are isolated. The isolated mitochondria are then extruded through a porous membrane so as to form particles having an average diameter of about 1 micrometer. These particles are then fixed onto a surface, with at least some amount of the particles being exposed or exposable to air exchange, thereby creating an air quality sensor.

EXAMPLE 2

Preparation of Another Air Quality Sensor

The present example discloses another method for preparing an air quality sensor. A collection of cells is gathered and the mitochondria from the cells are isolated. The isolated mitochondria are fractionated and sonicated to produce smaller particles, having an average diameter of about 2 micrometers. These particles are then fixed onto a gold coated surface, thereby creating an air quality sensor.

EXAMPLE 3

Preparation of Another Air Quality Sensor

The present example discloses another method for preparing an air quality sensor. A mixture of proteins, carbohydrates and lipids is prepared. The selection of proteins, carbohydrates and lipids is based upon the known presence of these proteins, carbohydrates and lipids in mitochondrial membranes. The mixture is sonicated and allowed to form a monolayer on a hydrophobic surface, thereby forming an air quality sensor.

EXAMPLE 4

Testing a Sample of Air

The present example outlines a method for sensing air quality. An air quality sensor that includes an isolated, de-energized, mitochondrial membrane is provided. A quantity of air to be tested can be gathered and then directed over the air quality sensor such that the air to be tested comes into contact with the membrane. While the air is in contact with the membrane, light having a wavelength of 430 nm is shown onto the membrane, and a wavelength of light emitted from the membrane is detected. The change in the wavelength of light detected (from that used for illumination) is then used to determine what molecules may be present in the quantity of air, e.g., by comparison with optical changes caused by known contaminants.

EXAMPLE 5

Testing a Sample of Air

The present example discloses another method for sensing air quality. An air quality sensor that includes numerous, de-energized, sensing particles is provided. Several quantities of air to be tested are gathered and then each quantity is directed over the air quality sensor at different locations, such that the air to be tested comes into contact with different mitochondrial particles. While the air is in contact with the particles, a broad spectrum of light having a wavelength of 300 nm to 600 nm is used to illuminate the particles. Changes in the wavelength of light emitted from the membrane, the lifetime of the fluorescence from the membrane, and photobleaching are monitored for each of the separate locations. These changes, once associated with the various amounts of air directed over the different locations, will provide one with information regarding the content and amount of various materials in the air sample. In the alternative, one can scan from 300 nm to 600 nm in increments of 1 nm, collecting data at each step, to determine the entire map of excitation/emission.

EXAMPLE 6

Sample Database

The present example outlines a method for developing an air contaminant database. An air quality sensor that includes a de-energized sensing particle is provided. Samples of air containing known amounts of contaminants are serially flowed over the sensing particle. As each sample comes into contact with the particle, the particle is illuminated with a broad spectrum of radiation and the optical properties of the radiation emitted from the particle are monitored as each sample having a different contaminant comes into contact with the particle. Both the final optical properties (of the particle when exposed to the contaminant) and the change in optical properties (from clean air to samples of air having known contaminants) of the particles can be recorded, correlated to their respective sample contaminant, and stored in a database. The optical properties examined will include one or more of: a) one or more wavelength of the emitted radiation, b) an intensity of the emitted radiation, c) Förster resonance energy transfer, d) photobleaching, or e) lifetime of the fluorescence. By performing these baseline control experiments and identifying the optical properties from these experiments, one can thereby create a library of optical signatures that can be used to identify various materials in air or other fluids.

EXAMPLE 7

Testing a Sample of Air by Dose Response Curves

The present example discloses another method for sensing air quality. An air quality sensor that includes numerous, de-energized, sensing particles is provided. An air sample is run over the sensing particle while the sensing particle is illuminated at 240 nm and monitored for radiation emission at 200 nm-500 nm. A dose response curve of the fluorescence of the sample is generated using at least three different doses of the sample of air. The generated dose response curve is compared to a library of dose response reference curves. Reference curves that are present in the dose response curve of the sample are identified, thereby identifying contaminants present in the sample.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A sensing particle comprising an isolated, de-energized, mitochondrial particle, wherein the mitochondrial particle has a diameter of about 0.01 micrometer to about 10 micrometer, and wherein the mitochondrial particle is covalently crosslinked to a semi-transparent or transparent surface.

2. The sensing particle of claim 1 wherein the mitochondrial particle has a diameter of about 0.05 micrometer to about 2 micrometer.

3. The sensing particle of claim 1 wherein the mitochondrial particle has a diameter of about 0.1 micrometer to about 0.4 micrometers.

4. The sensing particle of claim 1 wherein there is no significant proton gradient across an inner membrane of the mitochondrial particle.

5. The sensing particle of claim 1 wherein the mitochondrial particle comprises one or more heme groups and wherein at least 80% of the heme groups in the mitochondrial particle comprise an iron atom in the ferric state.

6. The sensing particle of claim 1 wherein the mitochondrial particle comprises at least one of the following: a lipid, a protein, or a carbohydrate.

7. An air quality sensor, the sensor comprising:
   at least one sensing particle comprising an isolated, de-energized, mitochondria' particle; and
   a semi-transparent or a transparent surface, wherein the at least one sensing particle is covalently cross-linked to the surface.

8. The air quality sensor of claim 7, wherein there are at least ten sensing particles attached to the surface.

9. The air quality sensor of claim 7 wherein the surface is configured to permit the transmission of radiation having wavelengths of about 200 nanometers to about 600 nanometers.

10. An air quality measurement device, the device comprising:
   an air intake port;
   a first air emission output configured to direct a quantity of air onto a location configured to receive an air quality sensor, wherein the air intake port is in fluid communication with the first air emission output;
   a first radiation source configured to emit radiation having a substantially uniform first wavelength onto the location;
   an air quality sensor at the location, wherein the air quality sensor comprises a mitochondrial particle; and
   a detector configured to measure a wavelength of radiation, an intensity of radiation, or the lifetime of the radiation, or all three emitted from the location.

11. The air quality measurement device of claim 10, the device further comprising:
   a second air emission output configured to direct a quantity of air onto a second location configured to receive the air quality sensor, wherein the air intake port is in fluid communication with the second air emission output.

12. The air quality measurement device of claim 11, wherein the second air emission output has a diameter that is different from a diameter of the first air emission output.

13. The air quality measurement device of claim 11, wherein the mitochondrial particle is attached to a semi-transparent surface or a transparent surface.

14. The air quality measurement device of claim 10 further comprising:
   a second radiation source configured to emit radiation having a substantially uniform second wavelength onto the location, wherein the second wavelength is about 200 nanometers to about 600 nanometers, and wherein the first wavelength and second wavelength are different.

15. A method of sensing air quality, the method comprising:
   providing a first isolated, de-energized, mitochondrial particle attached to a semi-transparent or transparent substrate;
   contacting the mitochondrial particle with a first quantity of air to be tested;
   applying a first amount of radiation to the mitochondrial particle;
   measuring an optical characteristic of the mitochondrial particle or radiation emitted by the mitochondrial particle; and
   correlating the optical characteristic with an air quality indicated by a presence of the optical characteristic.

16. The method of claim 15 wherein measuring the optical characteristic of radiation emitted by the mitochondrial particle comprises measuring at least one of: a) a wavelength of the emitted radiation, b) an intensity of the emitted radiation, c) Förster resonance energy transfer, or d) photobleaching; or e) lifetime of the fluorescence.

17. The method of claim 15, further comprising applying a second amount of radiation to the mitochondrial particle wherein the second amount of radiation has a substantially different wavelength than the first amount of radiation.

18. The method of claim 15 further comprising:
   providing a second isolated, de-energized, mitochondrial particle; and
   contacting the second isolated, de-energized, mitochondrial particle with a second quantity of air to be tested.

19. The method of claim 15 further comprising comparing the optical characteristic of radiation emitted by the mitochondrial particle to an optical characteristic of a known contaminant.

20. The method of claim 15, wherein the quantity of air to be tested comprises a known compound.

21. The method of claim 15, wherein the quantity of air to be tested comprises an unknown compound.

22. A method of making an air quality-sensing particle, the method comprising:
   providing a sample containing at least one mitochondria;
   extruding the mitochondria through at least one pore such that a mitochondrial particle is formed that has a diameter of about 0.5 micrometers to about 16 micrometers; and
   covalently crosslinking the mitochondrial particle to a semi-transparent or transparent substrate.

23. The method of claim 22, further comprising de-energizing the mitochondrial particle, thereby making an air quality-sensing particle.

24. The method of claim 23 wherein the mitochondrial particle is de-energized by contacting the mitochondrial particle with a reducing agent.

* * * * *

UNITED STATES PATENT AND TRADEMARK OFFICE
CERTIFICATE OF CORRECTION

| | | |
|---|---|---|
| PATENT NO. | : 8,904,851 B2 | Page 1 of 2 |
| APPLICATION NO. | : 13/696689 | |
| DATED | : December 9, 2014 | |
| INVENTOR(S) | : Manion | |

It is certified that error appears in the above-identified patent and that said Letters Patent is hereby corrected as shown below:

On the Title Page

Item (75), under "Inventor", in Column 1, Line 1, delete "Conulla" and insert -- Cronulla --, therefor.

Item (56), under "OTHER PUBLICATIONS", in Column 2, Line 8, delete "mitochondra" and insert -- mitochondria --, therefor.

Item (56), under "OTHER PUBLICATIONS", in Column 2, Line 20, delete "Forster" and insert -- Förster --, therefor.

In the Specification

In Column 3, Lines 39-40, delete "mitochodrial" and insert -- mitochondrial --, therefor.

In Column 6, Line 34, delete "340, 350." and insert -- 340, 380. --, therefor.

In Column 6, Line 39, delete "minors," and insert -- mirrors, --, therefor.

In Column 6, Line 48, delete "minors," and insert -- mirrors, --, therefor.

In Column 8, Lines 7-8, delete "fluorometery." and insert -- fluorometry. --, therefor.

In Column 9, Line 61, delete "and or" and insert -- and/or --, therefor.

In Column 13, Line 31, delete "(eg" and insert -- (e.g. --, therefor.

In Column 13, Line 37, delete "fluorometery" and insert -- fluorometry --, therefor.

Signed and Sealed this
Twenty-third Day of June, 2015

Michelle K. Lee
*Director of the United States Patent and Trademark Office*

CERTIFICATE OF CORRECTION (continued)
U.S. Pat. No. 8,904,851 B2

In the Claims

In Column 19, Line 3, in Claim 7, delete "mitochondria'" and insert -- mitochondrial --, therefor.